(12) United States Patent
Richwine

(10) Patent No.: US 7,386,970 B2
(45) Date of Patent: Jun. 17, 2008

(54) METHOD FOR DISPENSING TABLETS INTO A MULTI-COMPARTMENT CLINICAL REAGENT CONTAINER

(75) Inventor: Dean Charles Richwine, Elkton, MD (US)

(73) Assignee: Dade Behring Inc., Deerfield, IL (US)

( * ) Notice: Subject to any disclaimer, the term of this patent is extended or adjusted under 35 U.S.C. 154(b) by 3 days.

(21) Appl. No.: 11/556,265

(22) Filed: Nov. 3, 2006

(65) Prior Publication Data

US 2008/0105516 A1 May 8, 2008

(51) Int. Cl.
*B65B 5/10* (2006.01)
*B65B 35/30* (2006.01)

(52) U.S. Cl. .............................. 53/475; 53/543; 53/539; 53/247

(58) Field of Classification Search ................. 53/471, 53/475, 154, 158, 543, 539, 237, 247, 249; 198/436, 418.7, 419.1
See application file for complete search history.

(56) References Cited

U.S. PATENT DOCUMENTS

| | | | | |
|---|---|---|---|---|
| 2,190,620 A | * | 2/1940 | Milmoe et al. | 198/446 |
| 2,617,517 A | * | 11/1952 | Daniels | 198/419.1 |
| 2,955,393 A | * | 10/1960 | Muller et al. | 53/471 |
| 3,387,695 A | * | 6/1968 | Hendrickson | 198/383 |
| 4,150,751 A | | 4/1979 | Romagnoli | |
| 4,150,766 A | | 4/1979 | Westendorf et al. | |
| 4,308,942 A | | 1/1982 | Ackley | |
| 4,677,283 A | * | 6/1987 | Lewis | 235/98 C |
| 4,693,057 A | * | 9/1987 | Rittinger et al. | 53/539 |
| 4,744,492 A | | 5/1988 | Hackmann et al. | |
| 4,980,292 A | | 12/1990 | Elbert et al. | |
| 5,348,061 A | | 9/1994 | Riley et al. | |
| 5,522,512 A | * | 6/1996 | Archer et al. | 209/580 |
| 5,773,296 A | | 6/1998 | Montalbano et al. | |
| 5,927,546 A | | 7/1999 | Yuyama et al. | |
| 6,064,921 A | | 5/2000 | Pippin et al. | |
| 6,269,615 B1 | * | 8/2001 | Amborn et al. | 53/493 |
| D450,129 S | | 11/2001 | Wentz | |
| 6,311,462 B2 | * | 11/2001 | Amborn et al. | 53/493 |
| 6,394,308 B1 | | 5/2002 | Yuyama et al. | |
| 6,478,185 B2 | | 11/2002 | Kodama et al. | |
| 6,568,151 B2 | * | 5/2003 | Buckley et al. | 53/240 |
| 6,644,460 B2 | | 11/2003 | Gertitschke et al. | |
| 6,820,498 B2 | | 11/2004 | Kalbermatten | |
| 6,824,011 B1 | | 11/2004 | Woempner | |
| 6,849,457 B1 | | 2/2005 | Babson et al. | |
| 6,898,919 B2 | | 5/2005 | Kim | |
| 6,925,782 B2 | * | 8/2005 | Aylward | 53/475 |
| 2004/0098950 A1 | * | 5/2004 | Kim et al. | 53/473 |
| 2005/0092660 A1 | | 5/2005 | Vasiadis | |

\* cited by examiner

*Primary Examiner*—Rinaldi I. Rada
*Assistant Examiner*—Paul Durand
(74) *Attorney, Agent, or Firm*—Leland K. Jordan

(57) ABSTRACT

A method for dispensing a desired number of oriented tablets from a bulk source into a well within a reagent container by moving the tablets by vibration into a number of parallel loading chutes and transfer chutes and displacing the desired number of tablets into a drop chute aligned over the well.

10 Claims, 15 Drawing Sheets

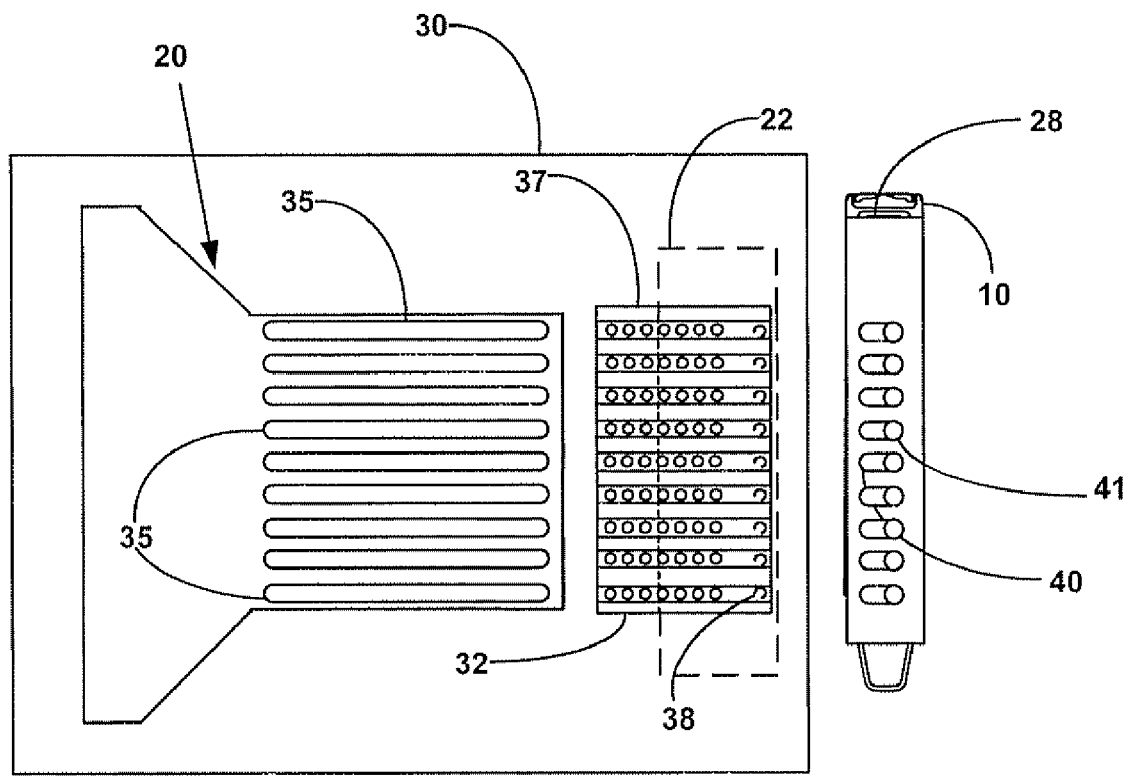
FIG. 6
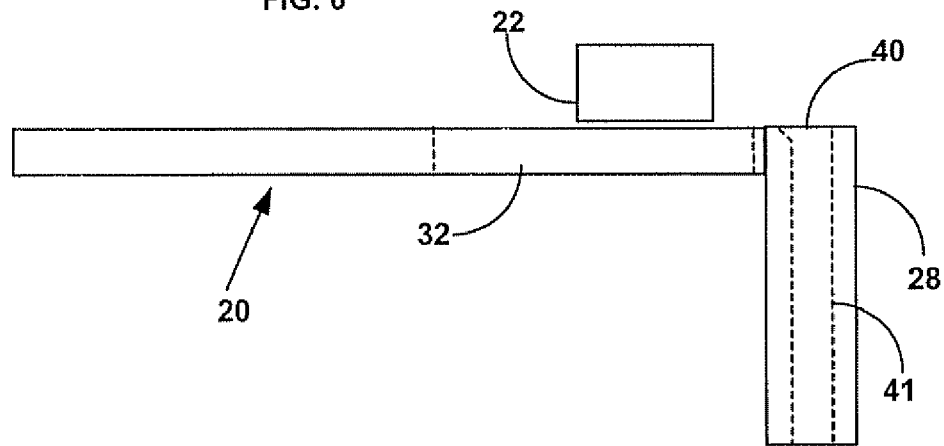
FIG. 6A
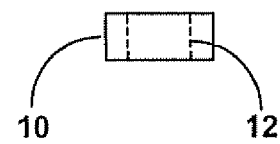

METHOD FOR DISPENSING TABLETS INTO A MULTI-COMPARTMENT CLINICAL REAGENT CONTAINER

FIELD OF THE INVENTION

The present invention relates generally to the dispensing of tablets, especially tablets used in the clinical analysis of biological samples. In particular, the invention relates to an apparatus for automatically dispensing multiple tablets into different wells within a multi-well reagent container.

BACKGROUND OF THE INVENTION

Automated clinical analyzers for determining the presence and levels of one or more selected analytes in relatively small biological liquid samples are widely used in hospital clinical laboratories. Preferred analyzers are equipped with an on-board supply of assay-specific reagents that are replenished by analyzing the assay demand pattern placed upon the analyzer. At a user selected time period before reagents within the analyzer's reagent inventory are exhausted, an alert message is provided so that appropriate measures may be undertaken to ensure an uninterrupted, timely supply of reagents.

For convenience and compactness within a chemical analyzer, it is desirable to store all reagents needed to conduct a single assay within contiguous compartments or vessels. Typical of such vessels is the multi-compartment or multi-well reagent container available for use in an analyzer known as the Dimension® Chemical Analyzer, sold by Dade Behring Inc., Deerfield, Ill. This multi-well container is in the form of a container strip like described in U.S. Pat. No. 6,943,030, and includes a rigid peripheral band formed integrally with each of several reagent containing wells so that the container strip generally tapers in a substantially elongated wedge-like manner from a first edge to a second edge.

To provide useful stability to the reagents between manufacture and use, it is sometimes necessary to lyophilize one or more reagents into a tablet form and to re-hydrate the tablets on-board an analyzer shortly before an assay is scheduled to be performed. During manufacture, a number of different reagent tablets may be placed in different wells within a multi-compartment reagent container and/or multiple numbers of the same tablet may be dispensed into the same well in order to provide the variety and quantity of reagent required to conduct an assay. For reasons of efficiency, it is desirable to automate the tablet loading process, however a number of obstacles are encountered during when transforming a bulk supply of tablets that have been lyophilized into carefully controlled numbers of different types of reagent tablets dispensed into specific ones of several reagent compartments.

A number of tablet dispensing devices are known, among them U.S. Pat. No. 6,478,185 that discloses a tablet vessel feed apparatus comprising a stock container for storing a plurality of tablet vessels, a vessel takeout section for taking out the tablet vessels from the stock container, and a conveyor for conveying the tablet vessels taken out from the stock container. This machine however is not suitable for dispensing into a multi-compartment container.

U.S. Pat. No. 5,348,061 discloses a tablet vessel feed apparatus applied to a tablet packing apparatus which has a plurality of feeder vessels containing different tablets respectively and packs the tablets discharged from each feeder vessel into a tablet vessel through a hopper. This machine is also not suitable for dispensing into a multi-compartment container.

U.S. Pat. No. 6,849,457 discloses a bead dispenser which is capable of preventing blockage or bridging of a bead receiving channel caused by a bottleneck of several biomaterial-coated beads at the inlet of the bead receiving channel using a spring mechanism which contacts and agitates the biomaterial-coated beads within the bead holding chamber.

U.S. Pat. No. 6,824,011 discloses a pellet dispensing device includes a rotatable cylinder having a plurality of chambers and a trigger mechanism for dispensing pellets one at a time but not simultaneously U.S. Pat. No. 6,820,498 discloses an apparatus which enables orientation of tablets introduced into a measuring station of a tablet tester.

These and other publications are related to dispensing of single tables but none are suitable for automatically and/or simultaneously dispensing multiple tablets into different wells within a multi-well reagent container.

SUMMARY OF THE INVENTION

The present invention provides a method to automatically dispensing tablets from a bulk supply into specific wells within a multi-compartment reagent container, the method comprising: (1) dispensing tablets from a bulk source onto a linear vibrating table; (2) orienting the tables to a flat position; (3) moving the tablets by vibration into a number of loading chutes; (4) moving the tablets by vibration into a number of transfer chutes; and, (5) displacing the desired number of tablets from the transfer chutes into a drop chute aligned over the specific wells, whereby the tablets are deposited into the wells.

BRIEF DESCRIPTION OF THE DRAWINGS

The invention will be more fully understood from the following detailed description thereof taken in connection with the accompanying drawings which form a part of this application and in which:

FIG. 6 is a top view of a tablet drop chute useful in the tablet dispensing system of FIG. 2;

FIG. 6A is an elevation view of the tablet drop chute of FIG. 6 aligned over the reagent container of FIG. 1 in a tablet stop position;

DETAILED DESCRIPTION OF THE INVENTION

Figure 1:
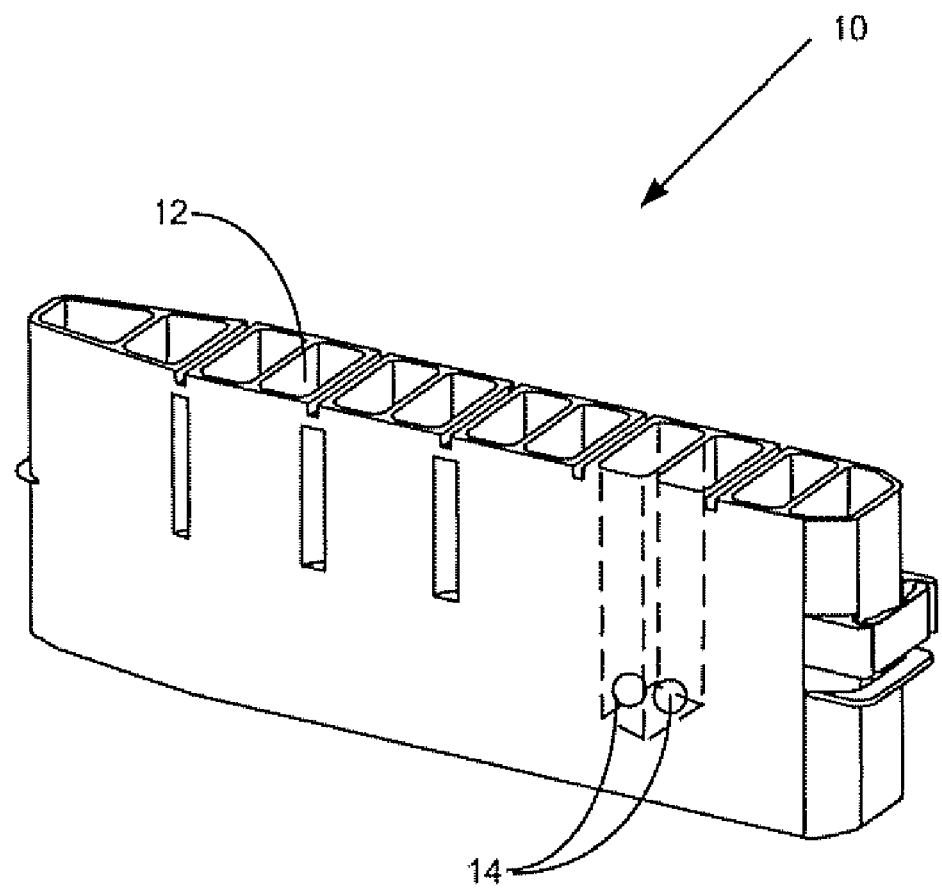
FIG. 1 is a perspective view of a reagent container useful when performing the present invention.
Figure 1A:
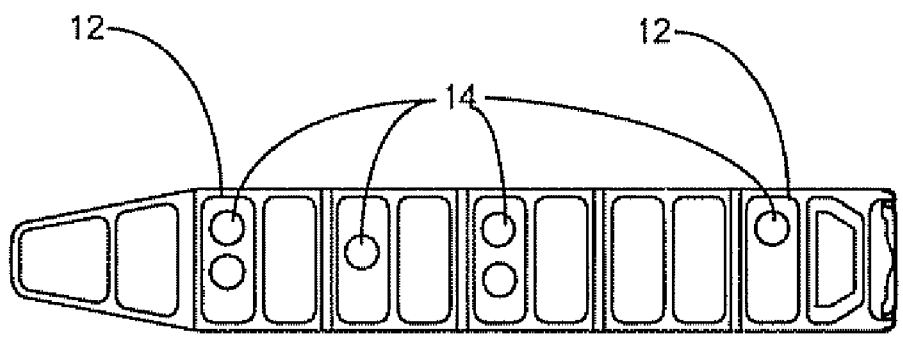
FIG. 1A is a top plan view of the reagent container of FIG. 1.

FIG. 1 illustrates a multi-compartment elongate reagent container 10 having a number of wells 12, each well 12 containing a few mL of a liquid reagent (not shown) or containing one or more reagent tablets 14 as necessary to perform a given assay. Container 10 has features to enable an analyzer to automatically determine whether a reagent container 10 is new and unused or whether the reagent container 10 has been previously used and possibly become contaminated whenever a reagent container 10 is initially placed onto an analyzer FIG. 1A is a top plan view of reagent container 10 illustrating an instance wherein two of the same reagent tablets 14 have been placed into two different wells 12 and wherein a single different reagent tablet 14 has been placed into two different wells 12 using a tablet loading apparatus exemplary of the present invention.

Figure 2:
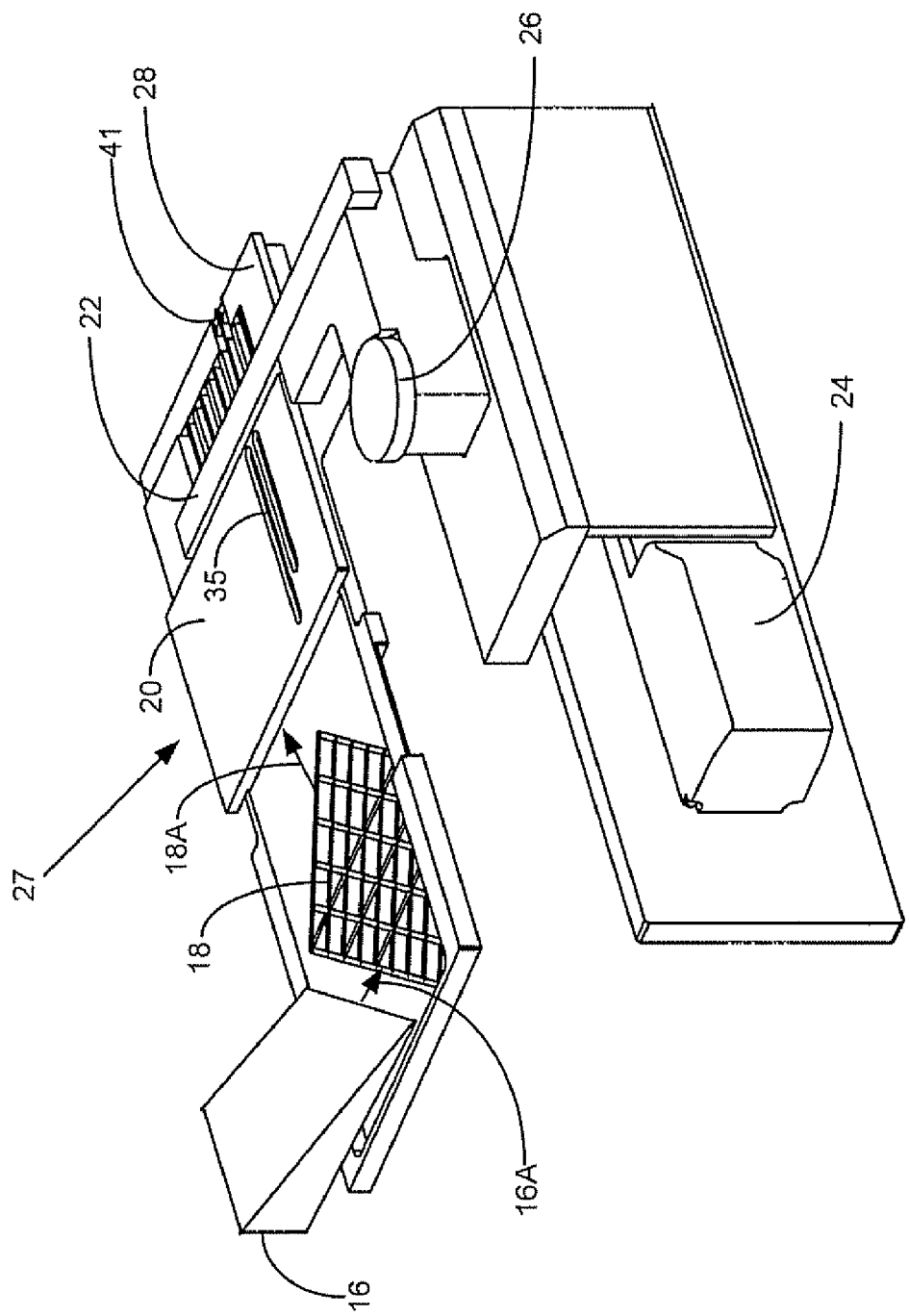
FIG. 2 is a perspective view of a system for dispensing multiple tablets into a multi-well reagent container, exemplary of the present invention.

FIG. 2 is a perspective of the tablet loading process of the present invention employing a bulk tablet dispenser 16 adapted to randomly translate tablets 14 to a tablet orienting table 18 as indicated by arrow 16A. Orienting table 18 comprises a tablet orienting zone 27 that orients tablets 14 into a flat orientation and, as indicated by arrow 18A, randomly translates these tablets 14 into a tablet guide plate 20 where tablets 14 are aligned in at least one open loading chute 35 sized to loosely contain a tablet 14. A tablet lift and load arm 22 is disposed above tablet guide plate 20 and is moveable by motor 24 in a plane parallel to the surface of tablet guide plate 20 and is also adjustable in height above the surface of tablet guide plate 20 by a threaded rod 26. As explained hereinafter, lift and load arm 22 is operable to selectively deliver a number of tablets 14 in at least one singulated row to a drop chute 28 having at least one open tapered openings 40 in the upper surface of drop chute 28, each tapered opening 40 leading to a vertically oriented chute 41 aligned above wells 12 within a reagent container 10 so that a requisite number of tablets 14 can be dropped into appropriate wells 12.

Figure 3A:
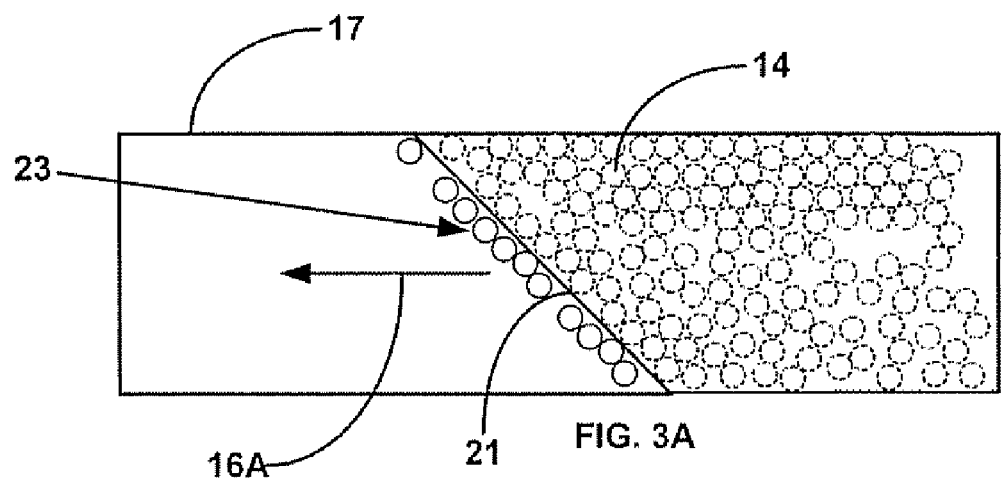
FIG. 3A is a top view of a bulk tablet dispenser useful in the tablet dispensing system of FIG. 2.
Figure 3B:
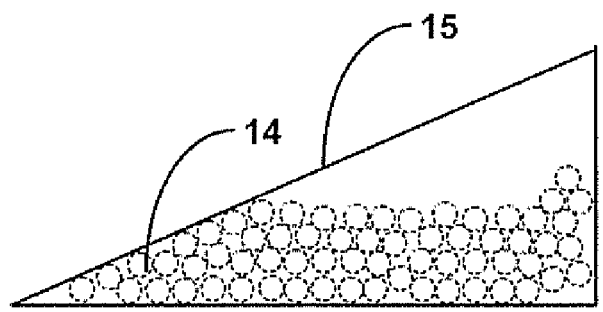
FIG. 3B is a side view of a bulk tablet dispenser useful in the tablet dispensing system of FIG. 2.
Figure 3C:
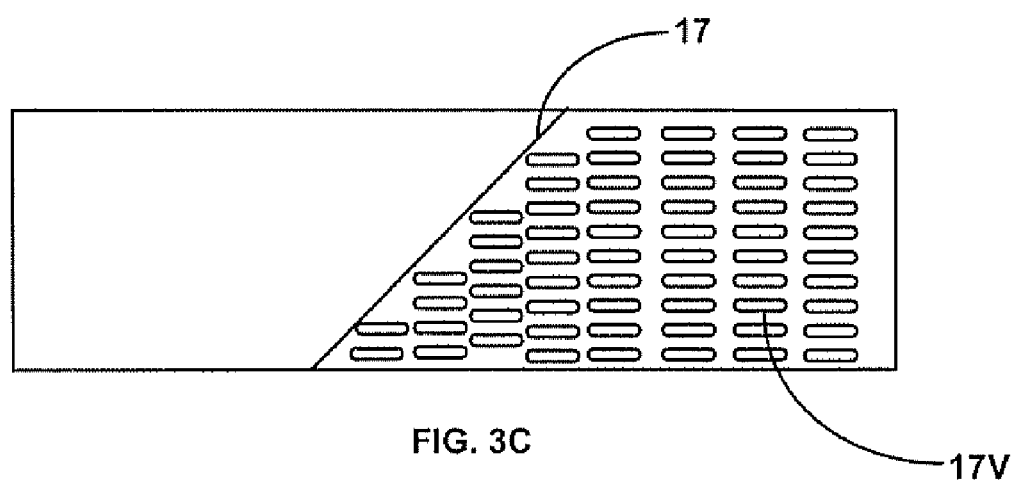
FIG. 3C is a bottom view of a bulk tablet dispenser useful in the tablet dispensing system of FIG. 2.

FIG. 3A is a top schematic illustration of a linear vibrating table 17 section of bulk tablet dispenser 16, linear vibrating table 17 having a 45-degree blade opening 21 and cantilevered so that tablets 14 (dotted line) move from a hopper 15 (side view schematic illustration in FIG. 3B) with bulk loaded tablets 14 therein in a 45-degree row 21 of tablets 14 towards tablet orienting table 18 as indicated by arrow 16A in FIG. 1 and FIG. 3A. FIG. 3C is bottom view schematic illustration of vibrating table 17 illustrating a number of vacuum openings 17V therein so that the flow supply of tablets 14 can be controlled (slowed down) and tablet 14 dust and fragmented tablets 14 removed by the application of vacuum from a conventional vacuum source (not shown). In essence, bulk tablet dispenser 16 is operable to deliver a controlled flow of tablets 14 in a relatively linear row 23 oriented at a 45-degree angle to the direction of tablet travel, tablets 14 being fed thereby from a bulk hopper 15 to a vibrating table portion 19 of tablet dispenser 16.

Figure 4:
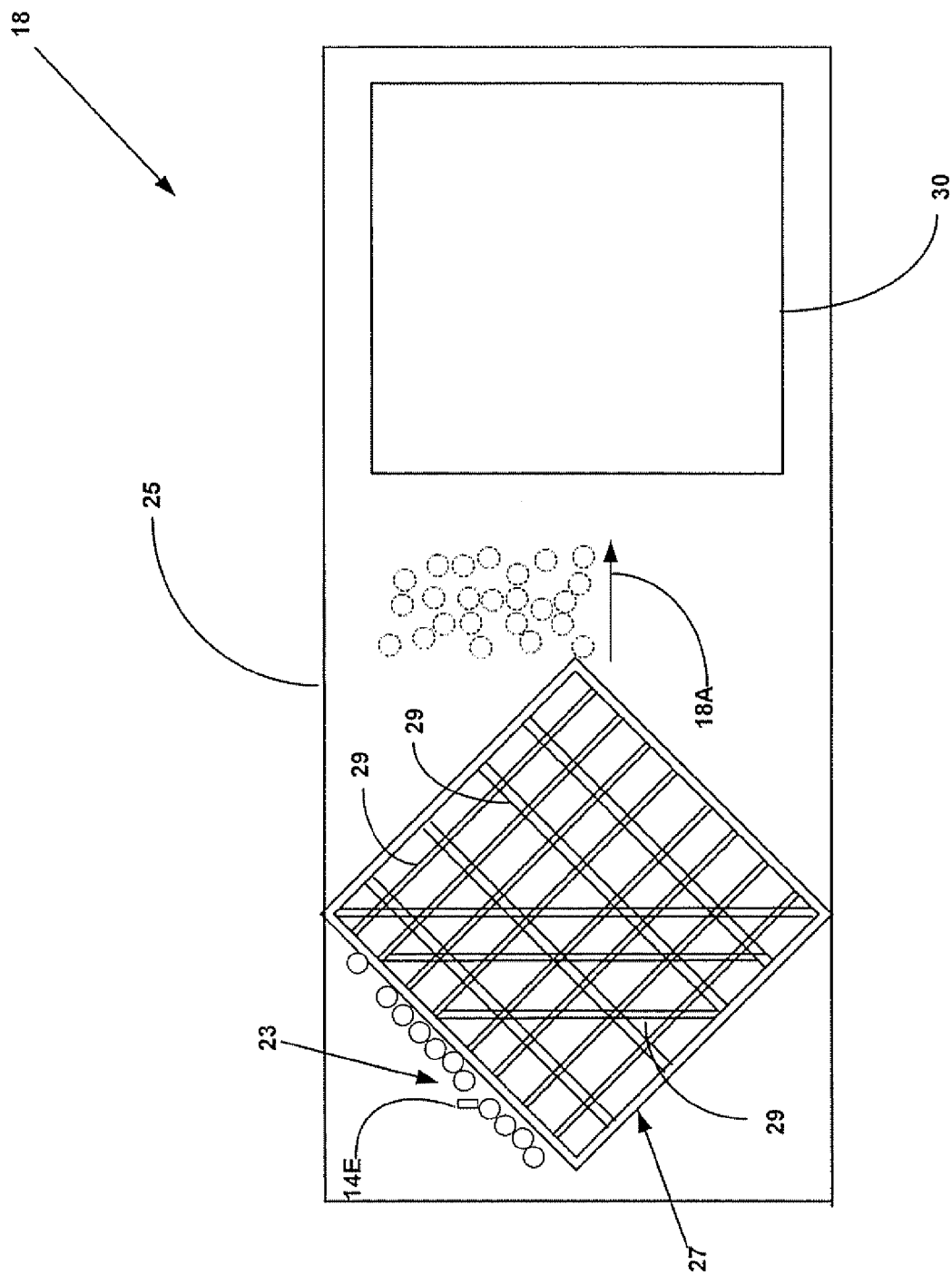
FIG. 4 is a top view of a tablet orienting and alignment table useful in the tablet dispensing system of FIG. 2.

FIG. 4 illustrates an important feature of the present invention, orienting table 18 comprising linear vibrating table 17 cantilevered so that tablets 14 move in a direction indicated by arrow 18A from a table orienting zone 27 towards a tablet alignment and transfer zone 30 described hereinafter Tablet orienting zone 27 comprises a number of vacuum grooves 29 formed in the upper surface of orienting and alignment table 18, vacuum groves 29 formed in a generally cross-hatched pattern. It has been discovered that as tablets 14 traverse across orienting zone 27, any tablets 14 not laying flat on orienting and alignment table 18 an in a edge orientation, like illustrated as 14E and in an edge orientation are caused to tip over and orient themselves in a flat position automatically without the necessity of using a conventional doctor blade. "Flat position" is intended to mean resting or laying on either of the two opposing larger, round diameter sides of a pill-shaped tablet 14, in contrast to standing on a circumferential edge of the tablet 14, tablets 14E. This feature advantageously eliminates the physical damage normally caused to tablets oriented by contact with such a doctor blade. It has also been discovered that optimum depth and spacing of vacuum groves 29 is dictated by the diameter of tablets 14; in an exemplary design, tablets 14 are powder compressed into a pill-shape of about 3/16-inch diameter with a height varying between 80 and 160-thousandths of an inch and the vacuum groves are about 0.025-inch deep at a spacing of about 0.375-inch. It has also been discovered that orientation of tablets 14 is most effective if the initial vacuum groves 29 engaging the 45-degree row 21 of tablets 14 (moving from vibrating table portion 19 towards tablet orienting table 18) is aligned parallel to the 45-degree row 21 of tablets 14 as illustrated in FIG. 4

Figure 4A:
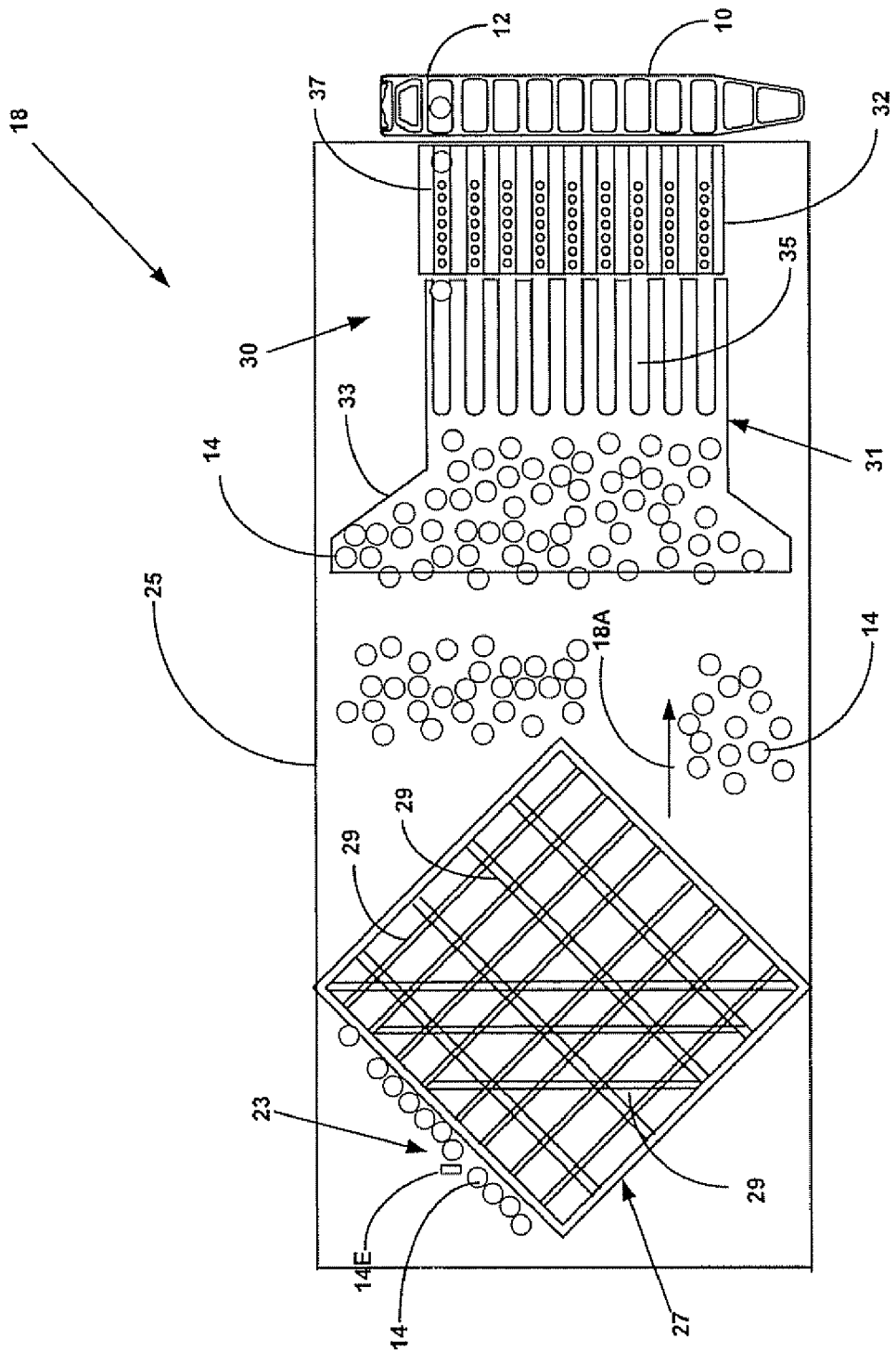
FIG. 4A is a top view of the tablet orienting and alignment table of FIG. 4 illustrating movement of tablets thereon.

FIG. 4A illustrates the progression of tablets 14 linearly vibrated across orienting table 18 and into a loading zone 31 within tablet alignment and transfer zone 30. Loading zone 31 is adapted to feed singulated rows of tablets 14 into a tablet transfer plate 32 having a number of transfer chutes 37 above a recessed vacuum supply system 32 (FIG. 9) ending near an exit portion of tablet transfer plate 32 where a reagent container 10 is proximately disposed during dispensing of multiple tablets 14 into different wells 12 within multi-well reagent container 10. As explained hereinafter, a number of different tablet guide plates 20 are sized to be positioned above vacuum supply system V described hereinafter (FIG. 9) and are configured to selectively direct at least one tablet 14 from at least one transfer chute 37 towards reagent container 10.

Figure 9:
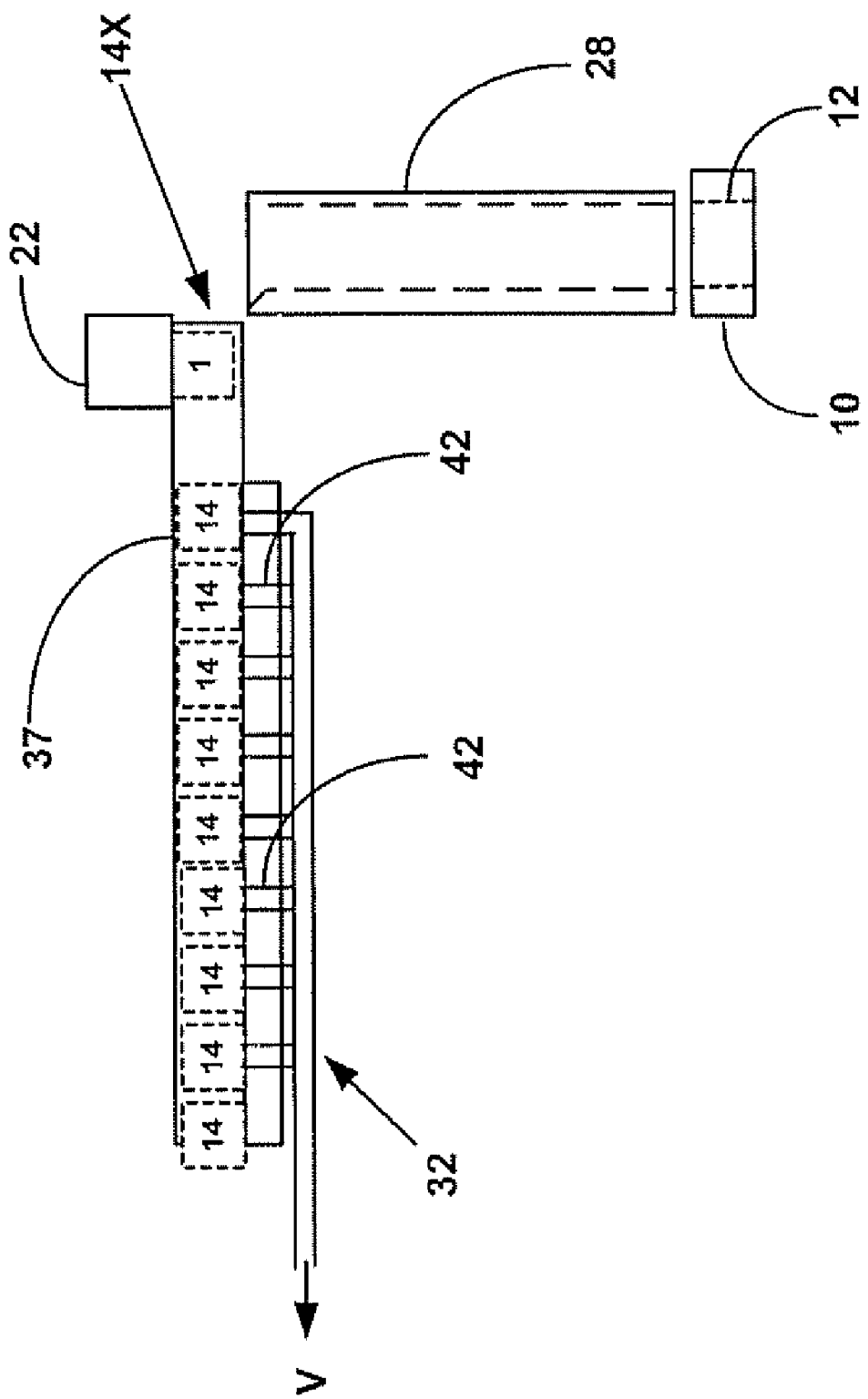
FIG. 9 is an elevation view of a vacuum supply system useful when loading a single tablet using the present invention.

FIG. 4A illustrates the progression of tablets 14 linearly vibrated across orienting table 18 and towards alignment zone 31 within tablet alignment and transfer zone 30. Alignment zone 31 is shown with a tablet guide plate 20 disposed within tablet alignment and transfer zone 30, the tablet guide plate 20 having a pair of inwardly tapered vertical edges 33 configured so as to direct the plurality of oriented tablets 14 towards a number of generally rectangular open loading chutes 35 sized to loosely contain a tablet 14 and formed in tablet guide plate 20, loading chutes 35 aligned parallel with one another and with an open end near an exit portion of alignment zone 31. A tablet transfer plate 32 having a number of transfer chutes 37 equal to the number of loading chutes 35 is positioned adjacent the exit portion of alignment zone 31, each transfer chute 37 having a number of vacuum openings 42 formed in the base thereof, the vacuum openings 42 in vacuum connection with a convention vacuum source V (FIG. 9). Each loading chute 35 is configured so that a vacuum port 42 is located beneath each of the tablets 14 within a transfer chute 35, vacuum ports 42 having vacuum applied thereto thereby controlling the number of tablets 14 that are dispensed into a well 12 of container 10. The number of transfer chutes 35 is made equal to the number of wells 12 in container 10 into which tablets 14 may be deposited and the spacing of transfer chutes 35 is likewise adjusted so that each of the loading chutes 35 is aligned with the center of wells 14. For purposes of understanding, tablet guide plate 20 is illustrated as having the number of transfer chutes 35 equal to the total number of wells 12 into which tablets 14 may be placed. For purposes of illustration only, a single dashed line tablet 14 is shown as being located in loading chute 35, transfer chute 35 and well 14. As explained hereinafter, the present invention provides a method for moving any number of such tablets 14 from bulk tablet dispenser 16 to orienting table 18 to loading chute 35 to transfer chute 35 and into well 14. In addition, a number of different tablet guide plates 20 and corresponding tablet transfer plates 32 are provided by the present invention, the different tablet guide plates 20 and tablet transfer plates 32 having equal and aligned numbers of transfer chutes 37 and loading chutes 35. The numbers of transfer chutes 37 and loading chutes 35 are selectively aligned with the different wells 12 into which at least one tablet 14 is to be deposited.

Figure 5:
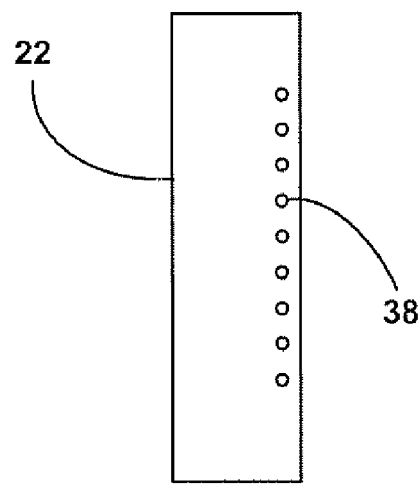
FIG. 5 is a bottom view of a tablet guide plate useful in the tablet dispensing system of FIG. 2.

Another important feature of the present inventive method for automatically dispensing at least one tablet 14 into at least one well 12 within a multi-well reagent container 10 is a tablet lift and load arm 22 disposed above tablet transfer plate 32 and moveable by motor 24 (see FIG. 2) in a plane parallel to the surface of tablet guide plate 20 and adjustable in height above the surface of tablet transfer plate 32 by a threaded rod 26. As seen in FIG. 5, a bottom surface view of lift and load arm 22, lift and load arm 22 is provided with a number of aligned vacuum suction ports 38, the vacuum suction ports 38 spaced apart a distance equal to the distance separating transfer chutes 35. Nine vacuum suction ports 38 are illustrated, however, as seen in FIG. 5B, the present invention provides a number of different lift and load arms 22, the different lift and load arms 22 having a variable number of vacuum suction ports 38 equal to and aligned with the previously described equal and aligned numbers of transfer chutes 37 and loading chutes 35, the numbers of transfer chutes 37 and loading chutes 35 being selectively aligned with the different wells 12 into which at least one tablet 14 is to be deposited.

Figure 5A:
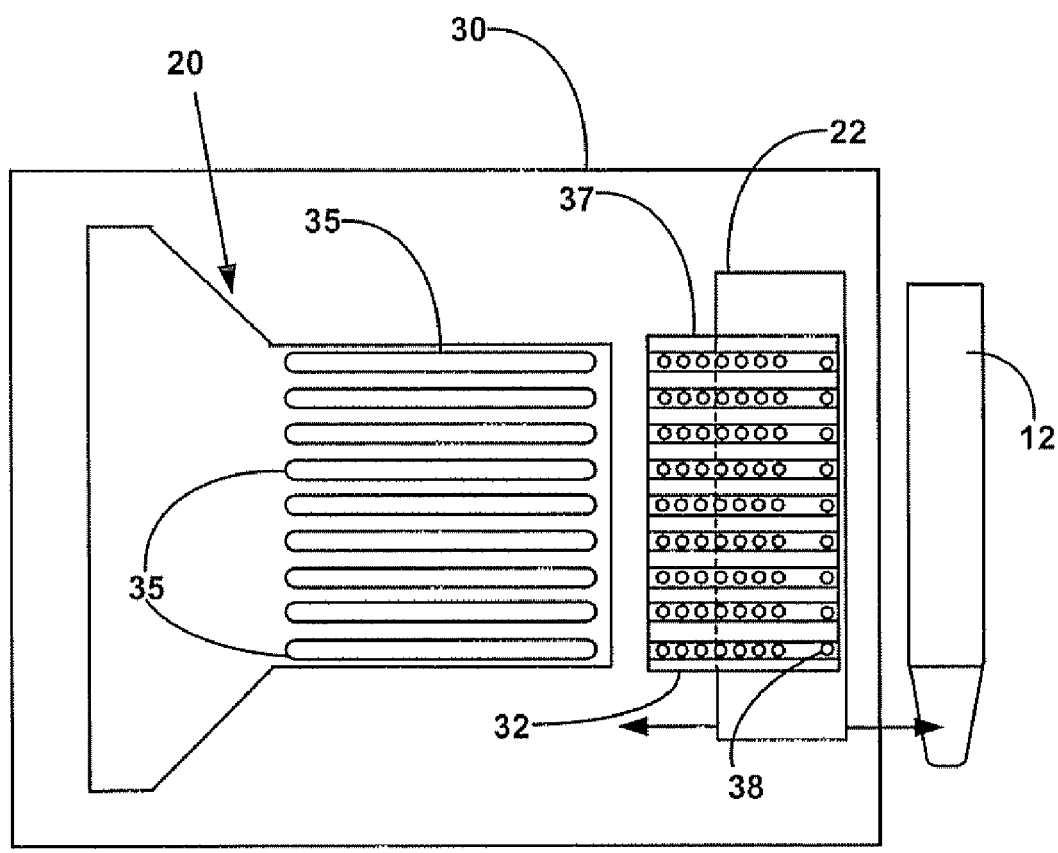
FIG. 5A is a spaced apart bottom view of the alternate tablet guide plate useful in the tablet dispensing system of FIG. 2.
Figure 5B:
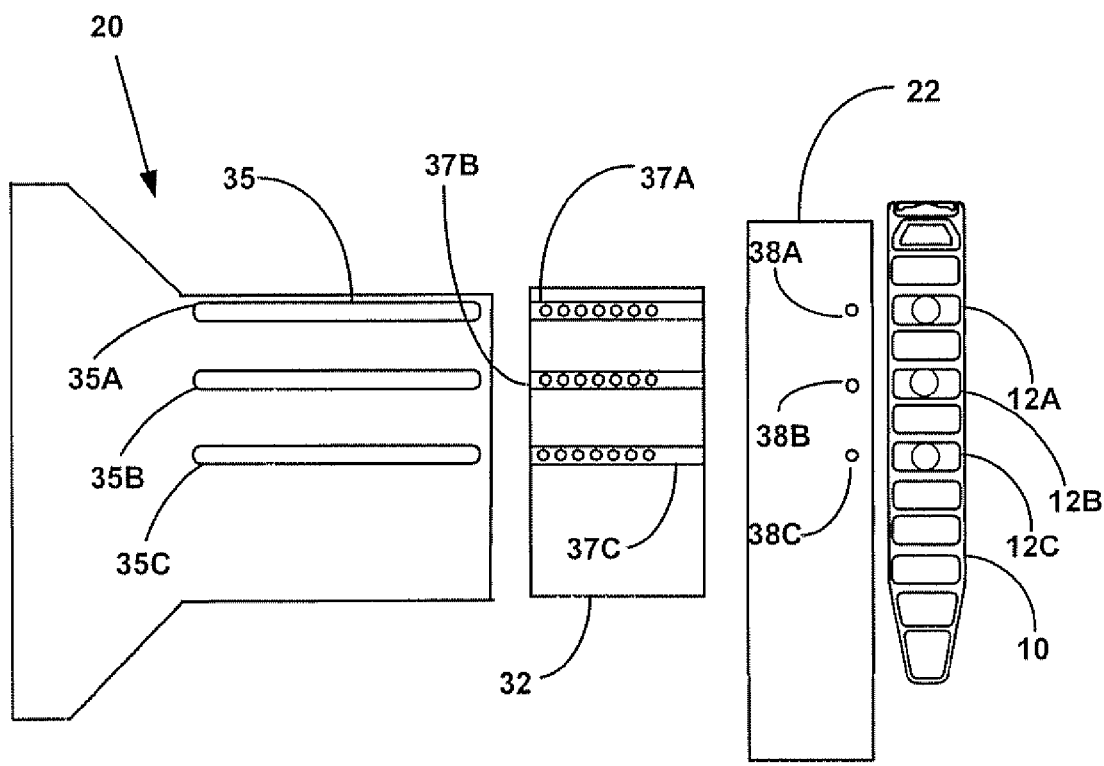
FIG. 5B is a spaced apart bottom view of the tablet guide plate of FIG. 5A.

As seen in FIG. 5A, a bottom surface view of lift and load arm 22, lift and load arm 22 extends perpendicularly across the totality of transfer chutes 35 within tablet transfer plate 32 and is provided with a number of vacuum suction ports 38 on the lower surface thereof, the suction ports 38 being vertically aligned with the center of selected vacuum ports 42 (FIG. 9). FIG. 5 is a schematic view from below the tablet guide plate 20 illustrating different numbers of vacuum suction ports 38 on the lower surface of lift and load arm 22 and aligned with the center of each vacuum port 42. In operation, a lift and load arm 22 like that illustrated in FIG. 5 would be suitable for simultaneously depositing tablets 14, usually a number of tablets 14 between one and three, into every one of the nine wells 12 illustrated in reagent container 10 that are aligned with the nine vacuum openings 36. Alternately, the tablet guide plate 20 illustrated in FIG. 5B, a spaced apart bottom view of tablet guide plate 20, tablet transfer plate 32, lift and load arm 22 is provided with a smaller number of aligned vacuum suction ports 38, the vacuum suction ports 38 spaced apart a distance equal to the distance separating transfer chutes 35. Nine vacuum suction ports 38 are illustrated in FIG. 5, however, as seen in FIG. 5B, the present invention also provides a number of different lift and load arms 22, for example a lift and load arms 22 having only three vacuum suction ports 38A, 38B and 38C for use with a tablet guide plate 20 having only three loading chutes 35A, 35B and 35C and a tablet transfer plate 32 having only three transfer chutes 37A, 37B and 37C and would be suitable for simultaneously depositing tablets 14 into only three wells 12A, 12B and 12C of the nine wells 12 illustrated in reagent container 10. Obviously, the number of and location of loading chutes 35 and transfer chutes 37 can be varied as desired to accommodate depositing tablets 14 into any of the wells 12 container 10 simply by changing the design of tablet guide plate 20 and tablet transfer plate 32.

Tablet lift and load arm 22 is disposed above tablets 14 a distance of about 0.010-inches and is moveable by motor 24 in a plane parallel to the surface of tablet transfer plate 32 as indicated by the opposing arrows; tablet lift and load arm 22 is furthermore adjustable in height over a distance of about 0.25-inches above the surface of transfer chutes 35 by a threaded rod 26 in order to accommodate tablets 14 of varying heights generally between 0.080 to 0.160 inches, as explained hereinafter.

Figure 6B:
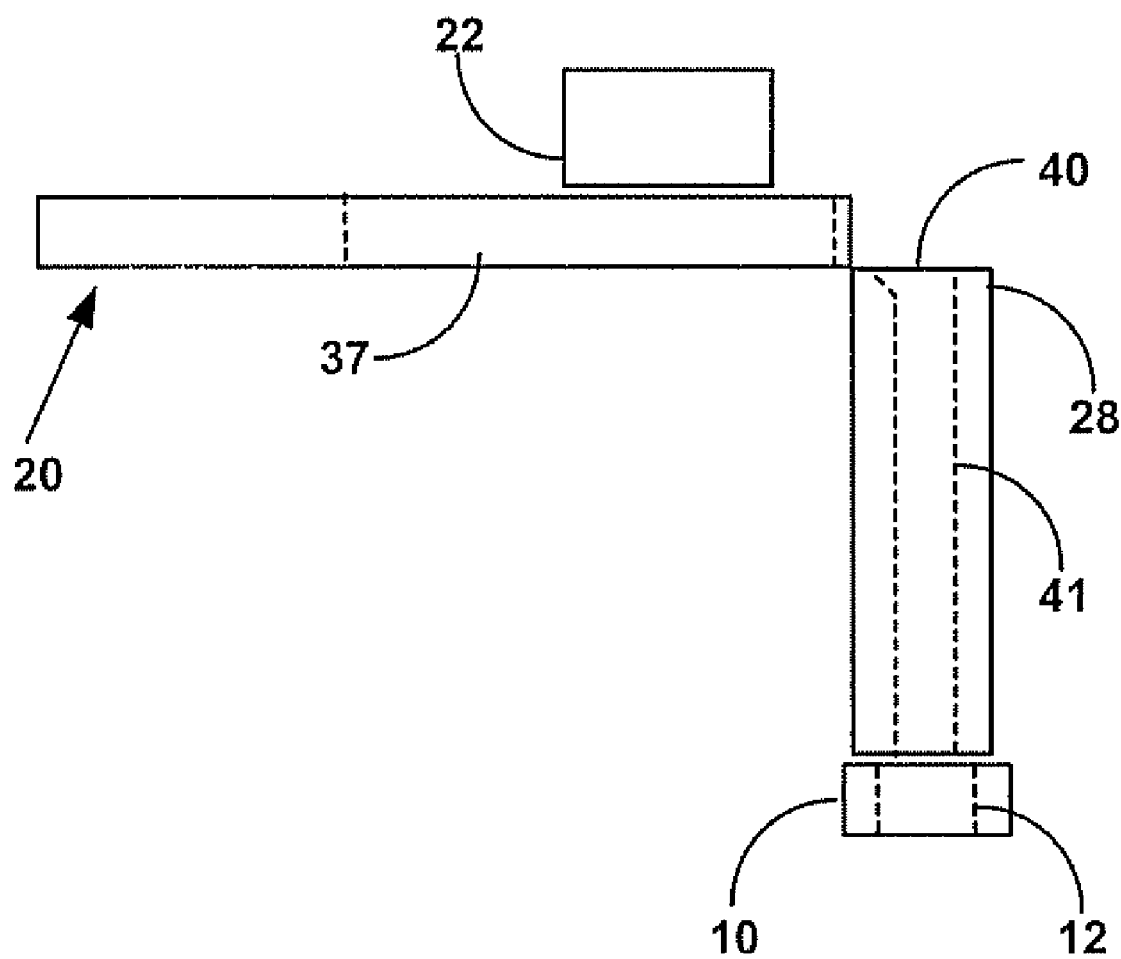
FIG. 6B is an elevation view of the tablet drop chute of FIG. 6 aligned over the reagent container of FIG. 1 in a tablet drop position.

Another feature of the present invention is a vertically translatable tablet drop chute 28 vertically aligned above a reagent container 10 so that a requisite number of tablets 14 selectively delivered by tablet lift and load arm 22 can be dropped by gravity into appropriate wells 12. This arrangement is illustrated in FIGS. 6 and 6A wherein it may be seen that drop chute 28 is operable to be positioned essentially level with tablet transfer chutes 37 in which position drop chute 28 acts to stop further movement of any tablets 14; drop chute 28 is also operable to be lowered a distance below tablet guide plate 20 to a tablet drop position like seen in FIG. 6B whereat tablets 14 in transfer chutes 37 may be pushed by tablet lift and load arm 22 into a number of tapered openings 40 in the upper surface of drop chute 28, each tapered opening 40 leading to a vertically oriented chute 41 oriented above wells 12 in reagent container 10.

Figure 7C:
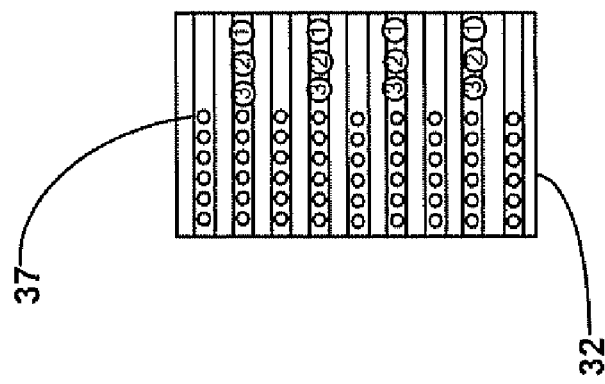
FIG. 7C is a top view of a tablet transfer plate having three loading chutes from which four tablets are displaced into the reagent container of FIG. 1.
Figure 7B:
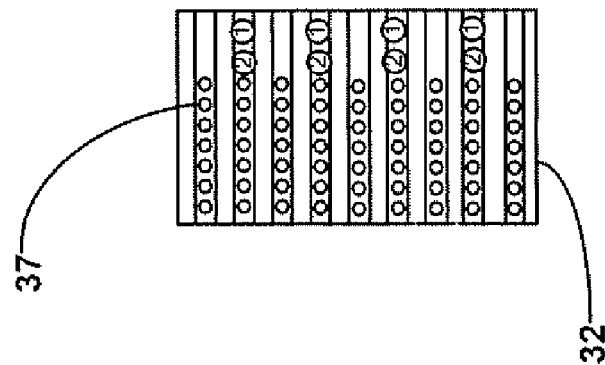
FIG. 7B is a top view of a tablet transfer plate having two loading chutes from which three tablets are displaced into the reagent container of FIG. 1.
Figure 7A:
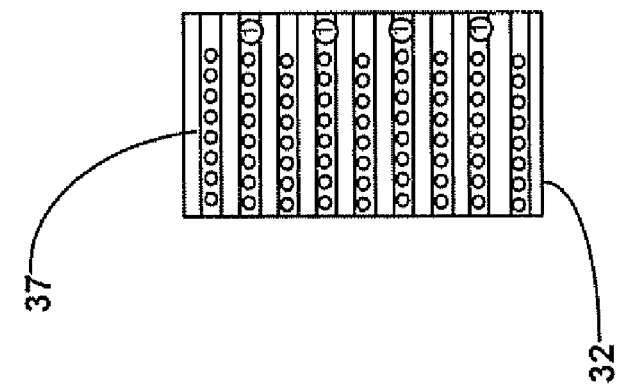
FIG. 7A is a top view of a tablet transfer plate having three loading chutes from which two tablets are displaced into the reagent container of FIG. 1.

To this point, tablet guide plate 20 has been shown and described as having a number of transfer chutes 37 basically equal to the number of wells 12 in which it might be desirable to have the same number of tablets 14 deposited; in clinical chemistry, however, different assays normally require different numbers of different tablets 14 in different wells 12 of a reagent container 10. In order to achieve its purpose, the present invention provides different transfer chutes 37 having different number of vacuum openings 42 formed in the base thereof, the vacuum ports 42 having vacuum applied thereto thereby to automatically dispose different numbers of tablets 14 into different wells 12 of a reagent container 10. This is illustrated in FIGS. 7A-7B-7C wherein the number of vacuum openings 42 decreases so that one, two or three tablets 14, respectively, are not constrained by vacuum at vacuum ports 42 and are therefore free to be deposited into wells 12, as explained below. To illustrate the numbers of "free" tablets 14 not constrained by vacuum at vacuum ports 42, tablets 14 marked "1", "2" and "3" are shown in alternating transfer chutes 37 so that the absence of vacuum ports 42 thereunder may be envisioned.

Figure 8:
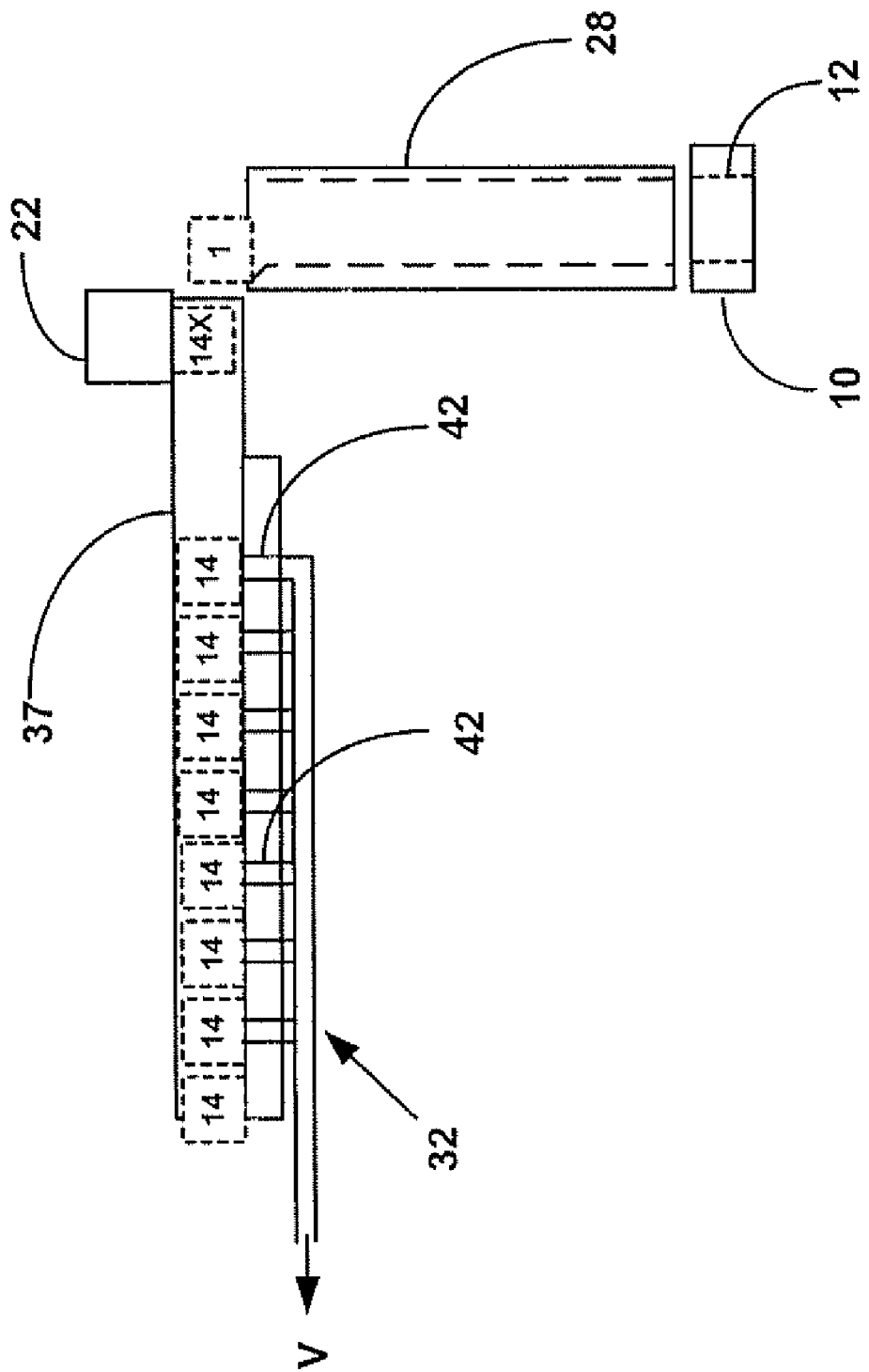
FIG. 8 is a top view of tablet dispensing system of FIG. 2 wherein the drop chute of FIG. 6 is in a tablet stop position.

Given the combination of FIGS. 4B and 5B and the descriptions thereof, for example, it should be apparent to an artesian that the progression of tablets 14 linearly vibrated across orienting table 18 and towards loading zone 31 and tablet guide plate 20 would provide a full complement of tablets 14 within the illustrative two loading chutes 35. This is illustrated in FIG. 8 where drop chute 28 is positioned as in FIG. 6A thereby acting as a stop wall against tablets 14. In order to load only two tablets 14, tablet lift and load arm 22 is translated by motor 24 so that a vacuum suction port 38 is vertically aligned over the second tablet, marked 14X, vacuum is applied to suction port 38 from a conventional source (not shown) and tablet 14X is lifted about 10 mils upwards above the surface of transfer chute 37. At this position, drop chute 28 is lowered by a conventional motor (not shown) to a tablet drop position as seen in FIG. 6B, and tablet lift and load arm 22 is translated towards drop chute 28 by motor 24 so that tablet 14X urges the next tablet 14 (marked 1 in FIG. 8) between tablet 14X and drop chute 28 into the tapered opening 40 leading to vertically oriented drop chute 41 oriented above well 12 in reagent container 10. Thereby, the first desired tablet 14 (marked 1 in FIG. 8) falls by gravity into well 12. Vacuum is then released from vacuum suction port 38 and tablet 14X also drops by gravity into tapered opening 40 and by gravity into well 12 after which, tablet lift and load arm 22 is returned to the "home" location 22H above transfer chute 37 and drop chute 28 is returned to its original upwards position (FIG. 6A) acting as a stop wall.

In order to control the number of tablets 14 to be deposited into wells 12, tablet transfer plate 35 is positioned above a vacuum supply system 32 like that seen in FIG. 9 and configured so that a vacuum port 42 is located beneath each of the tablets 14 within transfer chute 37 which are not to be moved towards drop chute 28 during the translation of tablet 14X towards drop chute 28, as illustrated in FIG. 9, showing an instance wherein one tablet 14X is being deposited into drop chute 28. Vacuum is applied from a vacuum source V prior to tablet 14X being affixed by vacuum to tablet lift and load arm 22 so that tablets 14 above vacuum ports 42 are constrained until lift and load arm 22 is returned to the "home" location 22H above tablet transfer plate 32 at which instance, vacuum is removed from vacuum ports 42 and tablets 14 are vibrated forward out of loading chutes 35 to uniformly fill transfer chutes 37.

Figure 10:
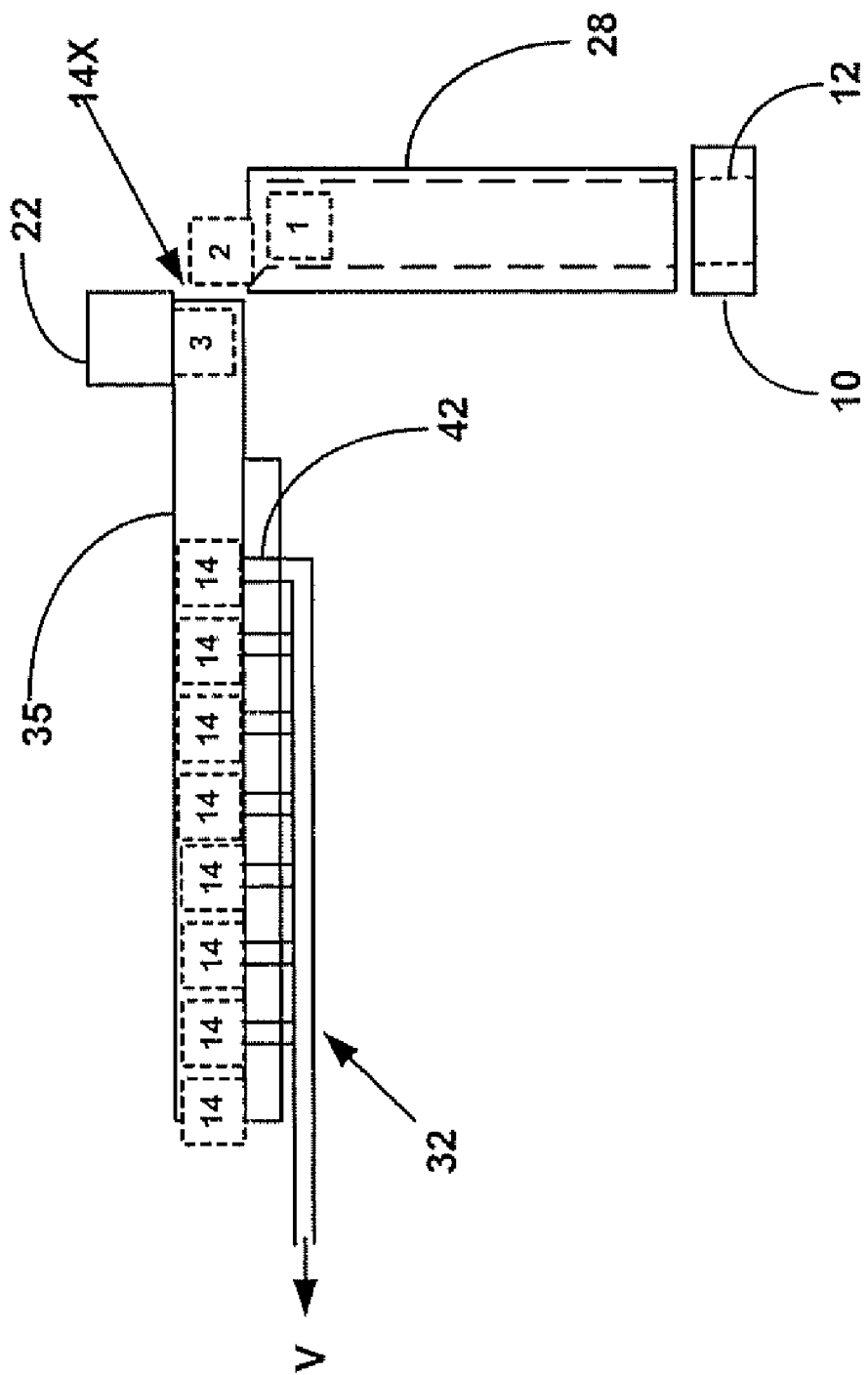
FIG. 10 is an elevation view of a vacuum supply system useful when loading three tablets using the present invention.

The above description of FIG. 8 concerns an instance wherein it is desired to deposit two tablets 14 into well 12; it is clear that other numbers of tablets 14 may be deposited into well 12 by the present inventive method for automatically dispensing multiple tablets 14 into different wells 12 within a multiwell reagent container 10 by changing the location at which tablet lift and load arm 22 lifts tablet 14X within tablet transfer chute 37. As an illustration, FIG. 9 depicts an instance wherein a single tablet 14X is desired to be deposited into a well 12 and FIG. 10 depicts an instance wherein three tablets 14 are desired to be deposited into a well 12. It should be understood that in these alternate instances, the number and location of vacuum ports 42 located beneath each of the "non-deposited" tablets 14 within tablet transfer chute 37 is correspondingly changed.

Figure 11:
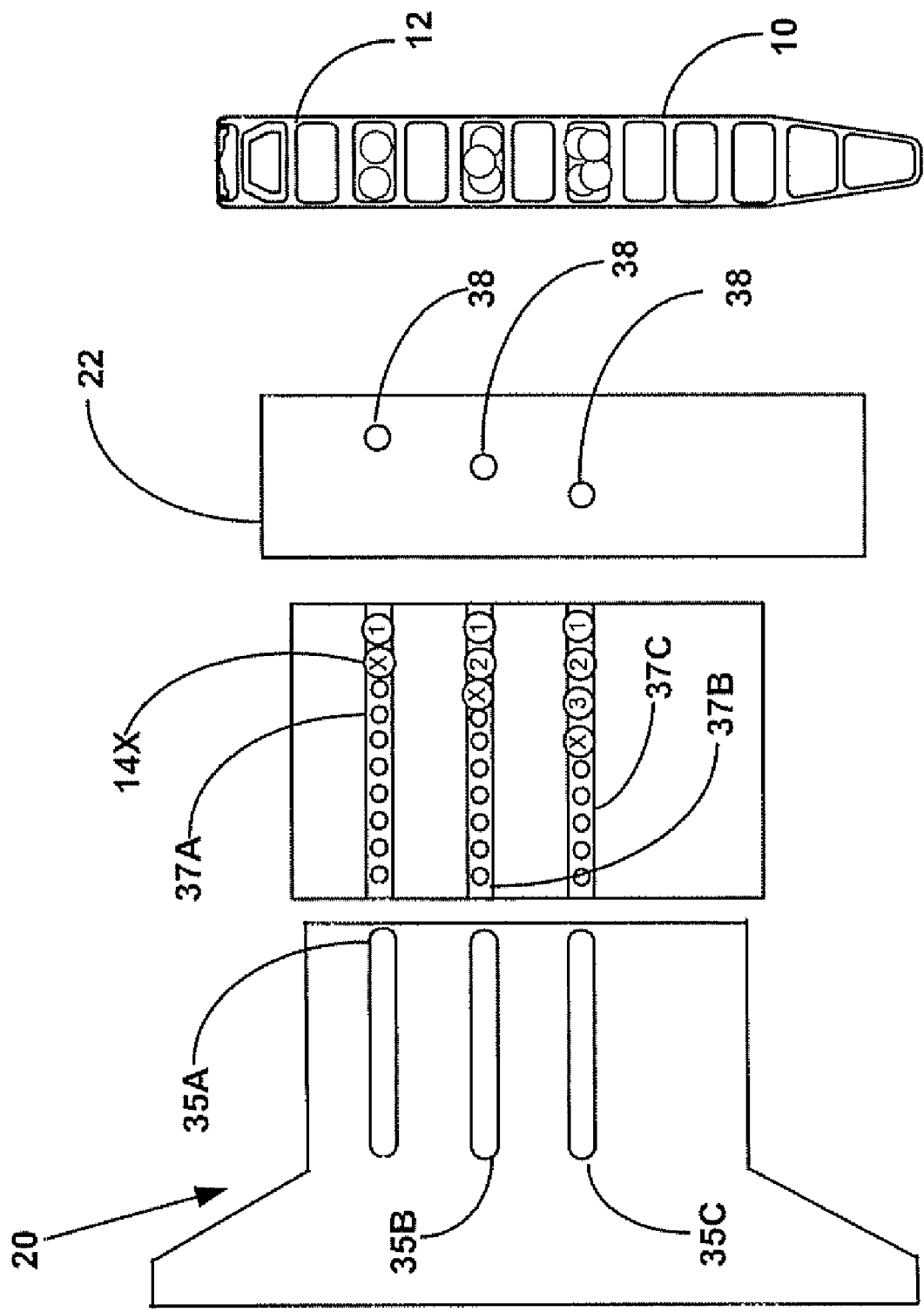
FIG. 11 is a top view of a tablet guide plate useful for simultaneously dispensing different numbers of tablets into different wells within the reagent container of FIG. 1; and, FIG. 12 is a top view of a tablet dislodging system and an optical inspection system useful when performing the present invention.

To this point, tablet guide plate 20 has been shown and described as having a number of loading chutes 35 equal to the number of wells 12 in which it is desirable to have at least one tablet 14; as described in conjunction with FIGS. 9, 10 and 11, the same number of tablets 14 have been deposited into different wells 12 of a reagent container 10. In an alternate embodiment of the present invention, tablet guide plate 20 has a number of loading chutes 35 and tablet transfer plate 32 has a number of transfer chutes 37 equal to the number of wells 12 in which it is desirable to have at least one tablet 14, however, the number of tablets 14 deposited into different wells 12 of reagent container 10 may be desired to be different. To accommodate such an instance, tablet transfer plate 32 is configured with different numbers of vacuum suction ports 42 located at different positions therein, as illustrated in FIG. 11. In FIG. 11, tablet transfer chute 37A is configured so that tablet 14X is located in a "second tablet location", tablet 14X to be lifted by tablet lift and load arm 22 and translated towards drop chute 28 by motor 24 so that the single tablet 14 (marked 1) between tablet 14X and drop chute 28 into the tapered opening 40 leading to vertically oriented chute 41 oriented above well 12 in reagent container 10, after which tablet 14X is also dropped into chute 41 as described above so that two tablets 14 are deposited within well 12. Similarly, tablet transfer chute 37B is configured so that tablet 14X is located in a "third tablet location", so that tablet 14X urges the two tablets 14 (marked 1 and 2) into chute 41 oriented above well 12, after which tablet 14X is also dropped into chute 41 as described above so three two tablets 14 are deposited within well 12. Additionally, loading chute 35C is configured so that tablet 14X is located in a "fourth tablet location", so that tablet 14X urges the three tablets 14 (marked 1, 2 and 3) into chute 41 oriented above well, after which tablet 14X is also dropped into chute 41 so four tablets 14 are deposited within well 12. Clearly, the location of tablet 14X can be adjusted so that any desired number of tablets 14 may be deposited into a well 12. Consequently, the present inventive method is seen to be useful for simultaneously dispensing different numbers of tablets 14 into different wells 12 within a multi-well reagent container 10.

Figure 12:
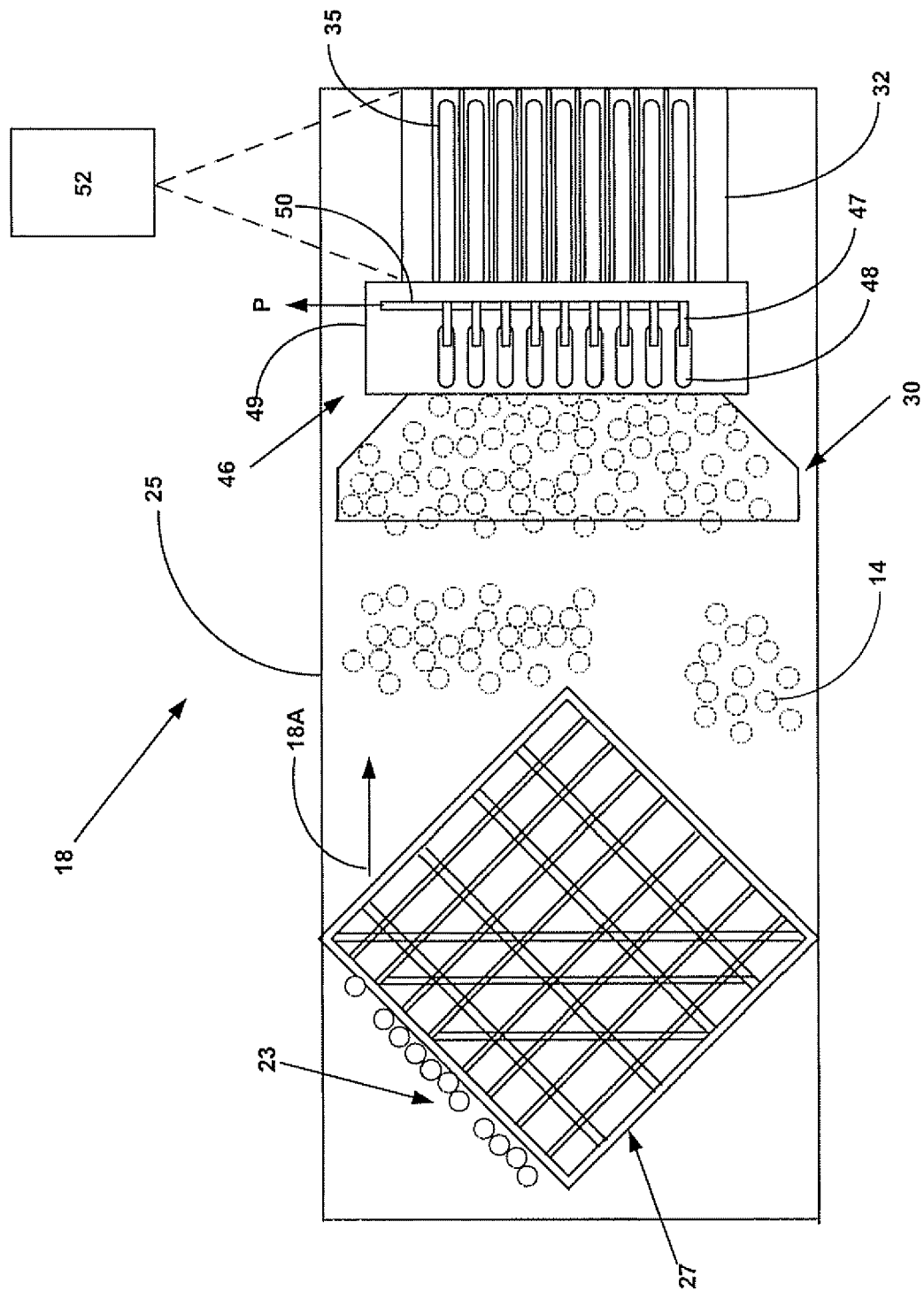

FIG. 12 illustrates a tablet dislodging system 46 configured to dislodge or disrupt tablets 14 than may become jammed together at the entrance to a loading chute 35 during the process of being translated by cantilevered linear vibrating table 25 from table orienting zone 27 towards loading chute 35 within tablet alignment zone 30. Dislodging system 46 comprises a number of air pressure tubes 47 oriented at about a 45-degree angle towards openings 48 in a plate 49, the pressure tubes 47 being connected by a pressure manifold 50 to a source of pulsed air P. Periodically during operation of vibrating table 25, pulsed air from source P is directed at tablets 14 through openings 48 in order to thereby prevent tablets 14 from becoming become jammed together.

Another feature of the present invention is a digital-camera based optical inspection system 52 positioned above tablet guide plate 20 in order to inspect loading chutes 35 to confirm the presence of a sufficient number of tablets 14 therein, to detect the presence of partial or broken tablets 14, to confirm that the desired number of tablets 14 have been moved into drop chute 28, to provide input into the operation of vibrating table 25 and the like.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A method for dispensing a desired number of tablets into individual wells within a reagent container, the method comprising:
    dispensing a plurality of tablets from a bulk source onto a linear vibrating table;
    providing a reagent container having individual wells;
    orienting the tablets to a flat position;
    moving the tablets by vibration into a number of loading chutes;
    moving the tablets by vibration into a number of transfer chutes;
    displacing the desired number of tablets from the transfer chutes into a drop chute aligned over the well, wherein displacing the desired number of tablets from the transfer chutes comprises lifting a first tablet within the transfer chute and moving said first tablet to urge tablets into the drop chute and thereafter, releasing said first tablet into the drop chute, whereby the tablets are deposited into the wells.

2. The method of claim 1 wherein orienting the tables to a flat position comprises moving the tablets by vibration across an orienting zone within the linear vibrating table, the orienting zone having a number of vacuum grooves formed in a generally cross-hatched pattern in the surface thereof.

3. The method of claim 1 wherein lifting said first tablet comprises applying a vacuum to said tablet, the vacuum applied by suction ports on the lower surface of an arm disposed above the loading chutes.

4. The method of claim 3 wherein moving said first tablet to urge the tablets into the drop chute comprises moving said arm above the loading chutes and toward the drop chute while said first tablet is lifted.

5. The method of claim 1 wherein a tablet dislodging system comprising a source of air pressure is located proximate the loading chutes and is configured and operated to dislodge tablets than may be jammed together.

6. The method of claim 1 wherein an optical inspection system is located above the loading chutes and is configured and operated to confirm the presence of tablets therein and to detect the presence of partial or broken tablets.

7. The method of claim 1 wherein the number of loading chutes and the number of transfer chutes is the same number as is the total number of wells within the container wherein tablets may be placed.

8. The method of claim 1 wherein the number of loading chutes and the number of transfer chutes is less than the total number of wells within the container wherein tablets may be placed.

9. The method of claim 1 wherein the same number of tablets is displaced into each drop chute.

10. The method of claim 1 wherein a different number of tablets are displaced into each drop chute.

* * * * *